(12) United States Patent
Carter et al.

(10) Patent No.: US 7,881,801 B2
(45) Date of Patent: Feb. 1, 2011

(54) MEDICAL DEVICE TESTING APPARATUS

(75) Inventors: Paul M. Carter, West Pennant Hills (AU); David J. Bull, Riverview (AU)

(73) Assignee: Cochlear Limited, Macquarie University, NSW (AU)

( * ) Notice: Subject to any disclaimer, the term of this patent is extended or adjusted under 35 U.S.C. 154(b) by 684 days.

(21) Appl. No.: 10/518,813

(22) PCT Filed: Jun. 27, 2003

(86) PCT No.: PCT/AU03/00827

§ 371 (c)(1),
(2), (4) Date: May 8, 2006

(87) PCT Pub. No.: WO2004/003580

PCT Pub. Date: Jan. 8, 2004

(65) Prior Publication Data

US 2007/0005118 A1    Jan. 4, 2007

(30) Foreign Application Priority Data

Jun. 28, 2002  (AU) .................................... PS3226

(51) Int. Cl.
*A61N 1/00* (2006.01)
(52) U.S. Cl. .................... 607/57; 324/528; 324/537
(58) Field of Classification Search ......... 324/527–528, 324/537–539, 542, 71.1, 76.11, 76.75, 500, 324/522, 543, 546, 555, 654; 607/57, 136; 381/312; 702/108, 118, 121
See application file for complete search history.

(56) References Cited

U.S. PATENT DOCUMENTS

| | | | | |
|---|---|---|---|---|
| 3,700,966 A * | 10/1972 | Morrow | ....................... | 361/49 |
| 3,963,981 A * | 6/1976 | Vis | ............................ | 324/510 |
| 4,192,451 A * | 3/1980 | Swerling et al. | ............. | 714/732 |
| 4,532,930 A * | 8/1985 | Crosby et al. | ................. | 607/57 |
| 4,578,637 A * | 3/1986 | Allen et al. | .................. | 324/538 |
| 4,742,295 A * | 5/1988 | Nahman et al. | ............. | 324/133 |
| 4,862,070 A | 8/1989 | Ostertag | | |
| 5,280,251 A * | 1/1994 | Strangio | ..................... | 324/539 |
| 5,477,152 A * | 12/1995 | Hayhurst | .................... | 324/542 |
| 5,552,713 A * | 9/1996 | Rashidi | ...................... | 324/555 |
| 5,570,012 A | 10/1996 | Orense | | |
| 5,609,616 A * | 3/1997 | Schulman et al. | ............. | 607/56 |
| 5,790,896 A * | 8/1998 | Nguyen | ....................... | 710/72 |

* cited by examiner

*Primary Examiner*—Mark W Bockelman
*Assistant Examiner*—Roland Dinga
(74) *Attorney, Agent, or Firm*—Kilpatrick Stockton LLP

(57) ABSTRACT

An apparatus (30) that can test external components of a cochlear implant system in a manner that does not require the person conducting the test to have advanced knowledge of the operation of the tested component. The apparatus provides a relatively quick and straightforward answer to the question of whether the component is operative or not. The testing apparatus (30) comprises at least one testing station (32,33,34) for receiving the component to be tested and makes an electrical and/or inductive connection thereto. A testing circuit is adapted to apply at least one test to the component and measure the response of the component to that test. The apparatus (30) compares the response of the component to stored data indicative of the response to the test of at least one equivalent component that is known to be operational and outputs a result of said comparison.

26 Claims, 5 Drawing Sheets

MEDICAL DEVICE TESTING APPARATUS

The present invention is a device to assist in testing the functionality of medical devices, such as external equipment associated with an implantable device. More preferably, the present invention is a tool to assist in the diagnosis, analysis and servicing of a cochlear implant system.

DESCIPTION OF THE PRIOR ART

Over recent times, the use of implantable devices to assist in restoring functionality to individuals who have lost the capability for that function to be performed naturally by the body has become increasingly common. Examples of such devices include pacemakers, defibrillators, cochlear implants, hearing aids and functional electrical stimulation (FES) devices.

A typically key component of currently available implantable devices has been the presence of an external controller unit to control the implantable portion of the device. This external controller unit can communicate with the implantable device through a variety of means to deliver various forms of control signals to allow the implantable device to perform its desired function.

With regard to cochlear implants, such devices have proven successful in restoring the sensation of hearing to individuals who have previously been considered as being severely or profoundly deaf, and unable to obtain benefit from conventional hearing aid devices. In such individuals, the hair cells of the cochlea have been damaged and are no longer able to transfer the mechanical vibration of the fluid inside the cochlea into electrical signals to be perceived by the brain as sound. One such cochlear implant device that has proven successful in such cases is described in U.S. Pat. No. 4,532,930, the contents of which are incorporated herein by reference. In such a device the cochlear implant bypasses the role of the hair cells and directly delivers electrical stimulation to the nerves in the cochlea, the electrical stimulation being representative of speech and environmental sounds. The neural impulses generated by the electrical signals are then sent to the brain and interpreted as sound. The electrical stimulation is usually delivered to selected nerve sites within the cochlea by an array of electrodes, electrically connected to an implanted stimulator device.

The implanted stimulator device typically receives a coded sound signal from an external sound processor device, and this coded signal directs the implanted stimulator device to deliver the appropriate electrical stimulation to the appropriate stimulation site to reproduce the corresponding sound. The implanted stimulator is equipped with electronic circuitry and switches to allow stimulation to be delivered to a number of electrodes simultaneously or sequentially to provide detailed sound perception.

The external device provides a coded signal to the implanted stimulator via a transcutaneous link, such as a radio frequency (RF) link, and the coded signal is directly representative of the surrounding sound as detected by an external microphone. The external microphone may be mounted on the external device or may be remote therefrom but connected via a suitable link.

In general, the basic function of the external processor is to take the audio signal from the microphone and to process it according to a particular speech coding strategy, to produce a signal that contains stimulation information for the implant. In this regard, speech processors are quite patient-specific and whilst the system hardware is relatively common for all users, the software used as well as the benefits gained from different software packages varies considerably from patient to patient.

It can therefore be appreciated that for devices such as cochlear implants, successful operation of the device relies upon the external and implanted portions of the device working together to produce the desired functionality. Should any one part of the external or implanted hardware malfunction, the capacity of the device to perform its function is severely affected. In the case of cochlear implants, this could result in uncomfortable or unsafe stimulation, or more commonly, in the recipient losing the capacity to detect sound.

For this reason it is important that should a recipient experience problems with their device, they must feel confident that the problem can be quickly detected and where possible, resolved so that the device can be returned to normal operation with minimal inconvenience to the recipient.

At present, in the unfortunate event of a cochlear implant recipient experiencing a difficulty or malfunction causing them to lose system functionality, the recipient must contact a local clinic or agent that has been assigned to deal with such issues. The clinic or agent is in most cases familiar with the recipient's needs and requirements and has full records of the recipient's history and any past problems they may have experienced.

In most cases it has been found that the major source of system problems and faults is related to the external system components, namely the external cables connecting the various external components, as well as the external transmitter coil. This is primarily due to the fact that these components are exposed to everyday handling and exposure to the elements, and as such are more likely to suffer damage.

Currently, if a recipient reports a device as being faulty, the clinic or agent firstly checks the recipient's external equipment for malfunction. This is done by swapping the suspected faulty device with a known non-faulty device and assessing whether the problem has been resolved. This process is repeated for all cables and coils and as such the clinic must carry a stock of spare parts for every piece of external equipment, which is often not economically feasible for smaller clinics. Such a process is understandably time consuming and reduces the efficiency of the clinic to deal with important and more time intensive tasks, such as implant programming sessions.

The present invention aims to address these issues.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention provides a device that can relatively simply test the components of a medical device, such as the external components of an implantable system, and give a direct indication as to whether the component is functional or not. Such a device will be able to be used by the recipient of the device or a clinic to diagnose problems immediately and avoids the need for the clinic to spend unnecessary time diagnosing and correcting such simple problems and reduce the need for them to carry a stock of spare components for trouble shooting purposes.

According to one aspect, the present invention is a testing apparatus for testing at least one component of a medical device and diagnosing problems associated therewith, the testing apparatus comprising:

at least one testing station for receiving said at least one component and making an electrical and/or inductive connection thereto;

at least one testing circuit adapted to apply at least one test to said component and measure the response of the component to said test;

a memory means for storing data indicative of the response to said test of at least one equivalent component that is known to be operational;

a comparator means for comparing the response of said component to said test to said data and determining whether said response is at least substantially similar to said data; and an output means for outputting a result of said comparison.

In one embodiment, the medical device is a tissue-stimulating device having an implantable component. In one embodiment, the device can be a hearing prosthesis such as a cochlear implant system. In this embodiment, said at least one component that is to undergo testing preferably comprises a cable and/or a transmitter coil adapted to be connected to an external speech processor component of a cochlear implant system.

The testing apparatus preferably comprises a case having a first surface having the testing stations as defined herein.

In one embodiment, the testing apparatus is preferably adapted to test more than one type of component. For example, different speech processors can be adapted to operate with different cable and/or coil combinations. In different embodiments, the testing apparatus can be adapted to test two, three, four, or more types of cables and/or two, three, four, or more types of cable and coil combinations. Where the testing apparatus is capable of testing two different types of cable, the apparatus preferably has at least two testing stations for providing an electrical connection to said cables. Where the testing apparatus is capable of testing three or more cables, the testing apparatus preferably has at least three or more testing stations, and so on.

Each cable testing station, where there is more than one, is preferably adapted to test only one type of cable. Where there are two or cable testing stations, each station is adapted to test a different type of cable from that of the other cable test stations. Each cable testing station can comprise a socket provided in the first surface of the case and having a shape that is adapted to receive a plug of a particular cable design and no other. Each socket design preferably allows electrical connection to the cable under test.

Each testing apparatus can have a single coil testing station. In another embodiment, the testing apparatus can have two or more coil testing stations. The coil testing apparatus preferably comprises a planar area in the first surface of the case on which the tested coil can be placed. The planar area can have an indicia means provided thereon that provides an indication of where the tested coil should be placed to ensure an appropriate test of the tested coil is undertaken. In one embodiment, the indicia means can comprise a pictorial representation of a transmitter coil. Where the testing apparatus is able to test more than one coil design, the planar area can have more than one unique indicia means provided thereon. For example, the planar area can have different pictorial representations of the different coil types that can be tested using the apparatus.

The tested coil preferably has a magnet that aligns itself correctly on the coil test station via another attracting magnet positioned at or below the planar surface of the case. The attractive force between the magnets is preferably used to maintain the tested coil in the correct place for testing.

Each tested coil preferably has a cable extending therefrom that is also testable by the testing apparatus. In a preferred embodiment, a tested coil with a cable extending therefrom is tested by positioning the coil in the appropriate location on the planar surface and then inserting the other end of the cable into the appropriate cable test socket of the apparatus.

The testing apparatus is preferably capable of sensing the type of coil, cable, or coil and cable combination that is under test and then access from the memory means the appropriate stored data for use by the comparator means of the apparatus.

In a preferred embodiment, the testing apparatus includes a control means that controls the overall function of the apparatus. The control means can comprise a microcontroller. The microcontroller can further preferably act as the memory means for the testing apparatus. The microcontroller further preferably comprises a microprocessor having an analogue to digital converter (ADC) to digitise the measurements representative of the tested component. The microprocessor is further preferably adapted to run software that controls the operation of the testing apparatus.

In a preferred embodiment, the measurements from said one or more testing circuits are in the form of current and voltage levels.

It is envisaged that said data indicative of the response of said equivalent operational component is preferably in the form of voltage and current ranges associated with non-faulty cables and transmitter coils used in cochlear implant systems.

In a further embodiment, the memory means is programmable to enable the stored data to be upgraded and altered according to the design requirements of the components to be tested.

In a further embodiment, the output means comprises one or more lights that can be illuminated or turned off in response to the outcome of the test. In a preferred embodiment, a light illuminates if the tested component passes the test and fails to illuminate if the tested component is inoperative or faulty. In one embodiment, the light can be a light emitting diode (LED), such as red LED.

In one embodiment, the LED can be adapted to only illuminate only when the response of said tested component is determined by the comparator means to be identical to the response of said equivalent operational component. It is, however, more likely that the LED can be adapted to illuminate when the voltage and/or current response of said tested component is within a predetermined range of what are considered acceptable values for that component. The predetermined range might be a variation of plus or minus 1% of the expected response. Other percentage values can be envisaged, eg. plus or minus 5%, 10%, 20% and so on.

In operation, the microcontroller of the apparatus can send a signal to the coil testing circuit comprising a socket voltage driver that drives the coil preferably with an AC square wave voltage source at or near the resonant frequency of the coil. This resonant frequency is dependent on the type of coil being tested. For example, in some instances it may be near 2.5 or 5.0 MHz. A simple push-pull square wave voltage driver circuit, similar to those used in external speech processors can be used for this purpose.

If the coil and cable combination plugged into the device is correctly functioning, a coil in the testing circuit will preferably resonate through an inductive coupling between the tested coil and the coil testing circuit and the coil current will have a value determined by the coil impedance at its resonant frequency, which is typically a few tens of Ohms, or less. In testing the coil and cable combination in accordance with the present invention, the apparatus preferably monitors the coil current and if the current is found to be above an acceptable value, the coil and cable combination pass the test and the device indicates a "PASS" to the tester via illuminating the LED. If the coil and cable combination is found to be faulty (eg. the coil cable is broken, connector faulty etc) the device indicates a "FAIL" by not illuminating the LED, or alternatively, by emitting a "FAIL" signal via another indicator means. In the event of a failure, most coil and cable combinations either involve a complete failure of the circuit or a detuning of the circuit in some way. Therefore in these fault conditions, the amplitude of the coil current will be reduced below a predetermined threshold and the coil will be detected as having failed.

In a preferred embodiment, the testing circuit for the coil and cable in combination preferably comprises al voltage rectification and current sensing circuit that measures the compliance of the coil and cable combination and outputs the result to the microcontroller.

Where the compliance of a cable is to be tested, a DC potential can be placed on one cable lead and the potential of another lead of the cable can be measured. The other end of the cable is preferably plugged into a resistor load network connecting all the cable leads together. When all the cable's leads are functioning normally a specific voltage, determined by the resistor load network, is expected on the sensed lead. If a fault occurs (one line open circuit or shorted to another) this will change the current flow in the cable and cause the voltage in the sensed lead to change. The voltage is preferably sensed by digitising it using the microprocessor ADC with software used to determine whether the sensed value corresponds to a normal or a faulty cable. When a voltage is sensed which corresponds to a normal cable, the microprocessor can illuminate the LED in the manner as discussed above.

According to a second aspect, the present invention is a method of testing at least one component of a medical device and diagnosing problems associated therewith comprising the step of making an electrical and/or inductive connection between said component and at least one testing station of the testing apparatus as defined herein and performing a test on said component.

The present invention provides an apparatus that can test external components of a cochlear implant system in a manner that does not require the person conducting the test to have advanced knowledge of the operation of the tested component. It provides a relatively quick and straightforward answer to the question of whether the component is operative or not.

BRIEF DESCRIPTION OF THE DRAWINGS

Examples of the invention will now be described with reference to the accompanying drawings in which.

PREFERRED MODE OF CARRYING OUT THE INVENTION

Figure 1:
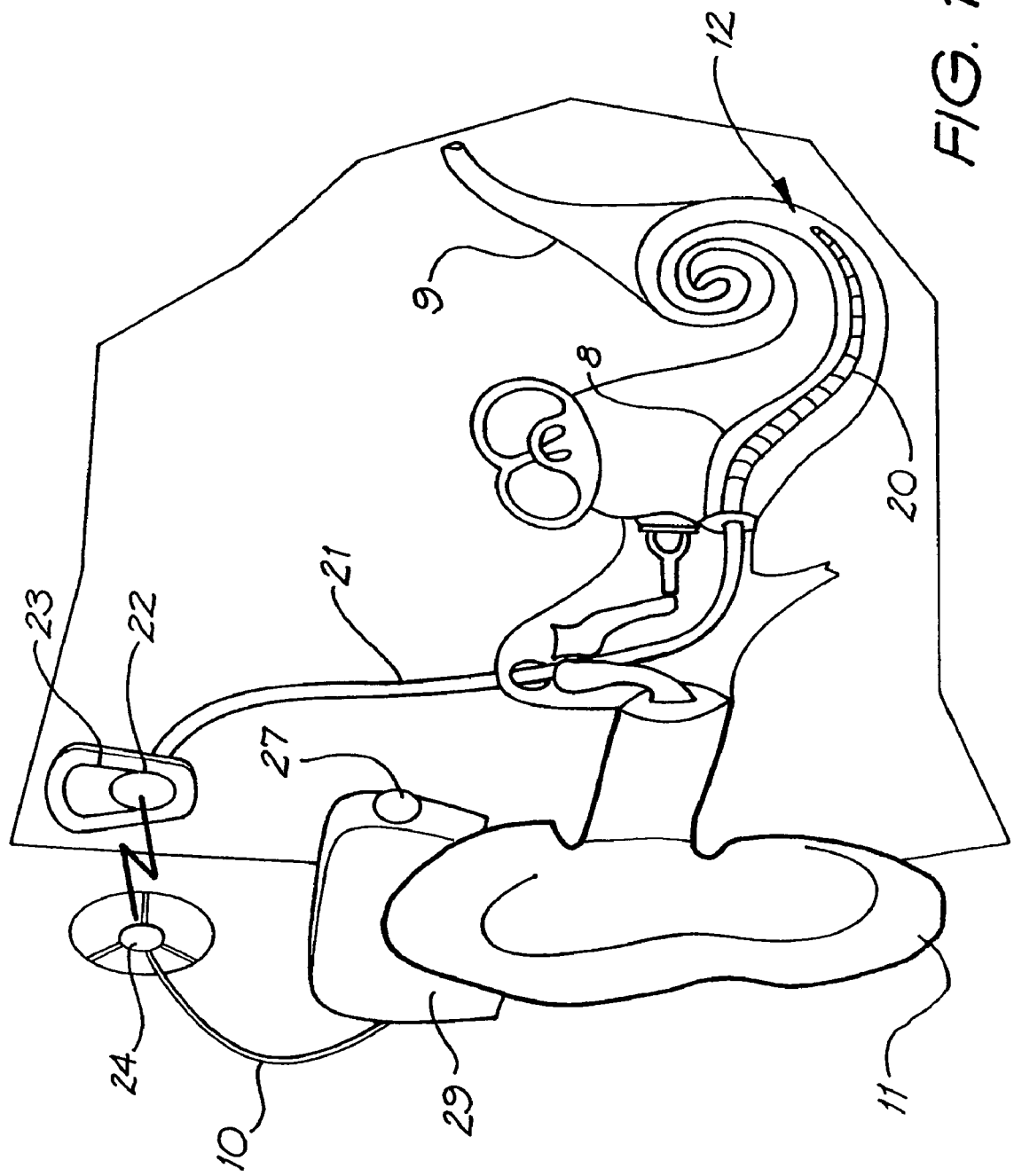
FIG. 1 is a pictorial representation of a conventional cochlear implant system.

Before describing the features of the present invention, it is appropriate to briefly describe the construction of a cochlear implant system with reference to FIG. 1.

Cochlear implants typically consist of two main components, an external component including a speech processor 29, and an internal component including an implanted receiver and stimulator unit 22. The external component includes an on-board microphone 27. The speech processor 29 is, in this illustration, constructed and arranged so that it can fit behind the outer ear 11. Alternative versions may be worn on the body. Attached to the speech processor 29 is a transmitter coil 24 which receives electrical signals through a cable 10 and transmits signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9. The operation of such a device is described, for example, in U.S. Pat. No.4,532,930.

The sound processor 29 of the cochlear implant can perform an audio spectral analysis of the acoustic signals and outputs channel amplitude levels. The sound processor 29 can also sort the outputs in order of magnitude, or flag the spectral maxima as used in the SPEAK strategy developed by Cochlear Ltd.

As previously mentioned, when a problem is reported by a cochlear implant recipient, the clinic responsible for identifying and resolving the problem, often follow a systematic approach. It is established that there may be a number of possible causes for the problem, such as a loss of implant function, and these causes may be related to:

the external hardware;
physiological or psychological changes; or
the implanted hardware.

As the external hardware is often the simplest and most obvious source of problems, the clinician often starts with assessing the external hardware for faults before consideration is given to the other two relatively more complicated problems.

In the case of the cochlear implant as described in FIG. 1, the main external components are the external sound processor 29, the transmitter coil 24, and the connector cable(s) 10. The present invention addresses a device and process to simply and quickly test the transmitter coil and connector cables for proper electrical function, such that the clinician or recipient can quickly solve such problems or eliminate the possibility of such problems being a contributing factor to the reported problem.

In terms of the transmitter coil and cables used in cochlear implants, their function is to transmit encoded radio frequency signals from the external speech processor to the internal component of the implant that is positioned beneath the recipient's skin. Therefore it is both the coil and cable that form part of the resonant RF circuit which is coupled to the receiver coil in the implant. The RF is typically generated at either 2.5 MHz or 5.0 MHz depending upon the design of the speech processor and implant. In operation, the transmitter coil and the receiver coil are tuned to frequencies, for example, close to but not exactly at, either 2.5 or 5.0 MHz.

In construction, the coils usually consist of a number of turns of wire, typically around 30mm in diameter, with an injection moulded plastic covering all components. In the centre of the coil there may be positioned a magnet that is used to locate and hold the transmitter coil in an appropriate external position relative to the implant or receiver coil, which also has a magnet positioned therewith.

In cochlear implants produced by the present applicant, depending upon the type of speech processor used, there may be a number of different transmitter coils designed to operate with each of the different speech processors that are or have been able to be used by cochlear implant recipients. These coils are often not compatible with processors other than that which they have been designed for, and hence interchanging of coils may result in the implant receiving no signal, a non-meaningful signal, or an incomplete or garbled signal. One way of overcoming the problem of using the wrong transmitter coil with the wrong processor has been to provide different electrical connecting plugs for each coil, matching with a particular type of socket in the speech processor. This has also resulted in the need for a wider variety of cables connecting the speech processor to the transmitter coil, with corresponding sockets to match the particular device.

Figure 2:
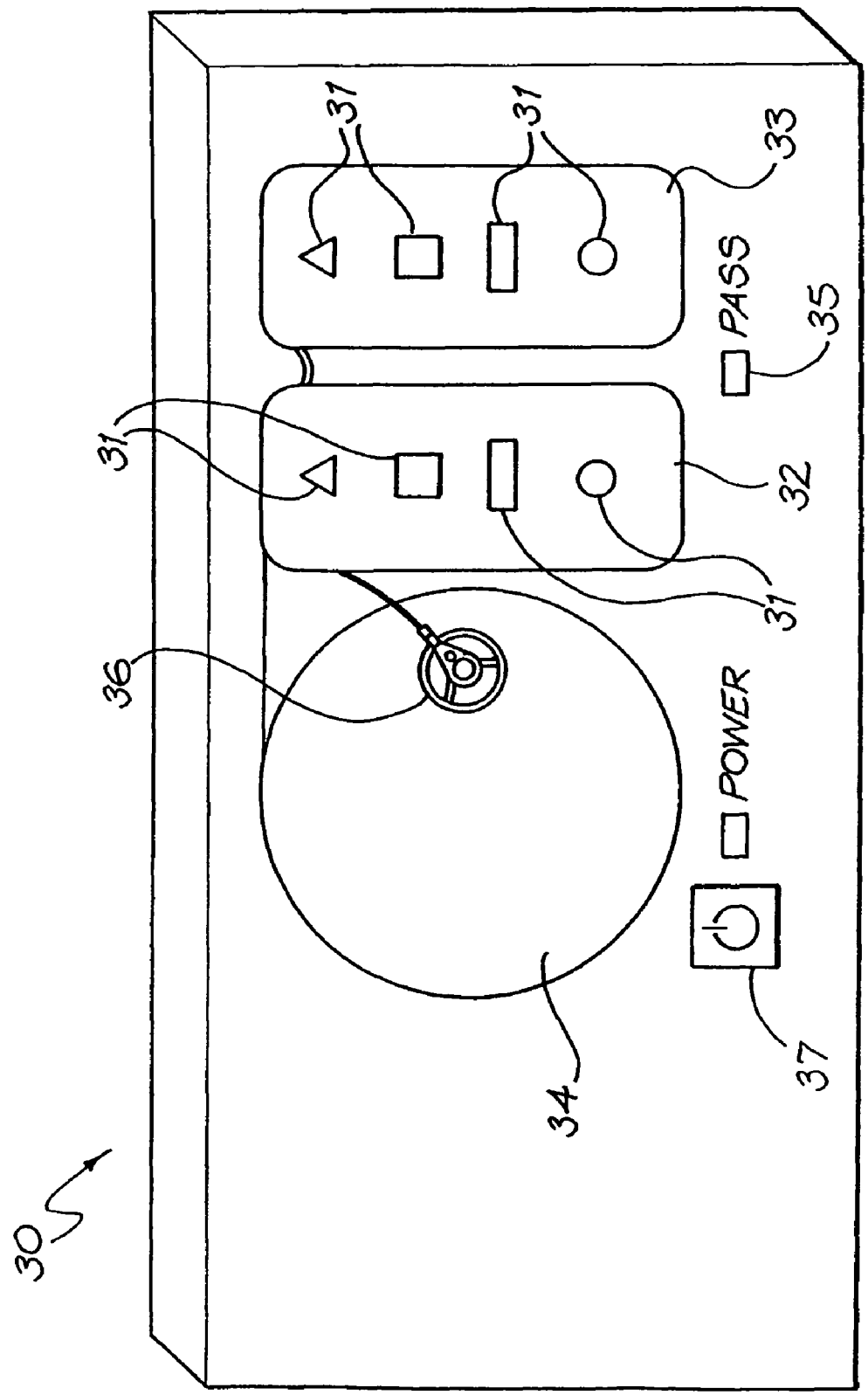
FIG. 2 is a pictorial representation of a tester unit in accordance with one embodiment of the present invention.

FIG. 2 is a top view of one embodiment of the present invention. The tester unit is represented as numeral 30 and includes a plurality of test stations designated by reference numerals 32, 33 and 34 arranged on the top surface of the unit 30 for testing the external coil and cables of a cochlear implant. In test stations 32 and 33, a plurality of connector sockets 31 are arranged as shown with each socket in test station 32 having a corresponding socket arranged in test station 33. The connector sockets 31 are designed to receive the various types of cables provided with the implantable system, with each free end of a cable having a plug that is connectable to the appropriate socket in test station 32 and 33, for testing. Each of the connector sockets 31 are designed to receive only one type of cable plug, to ensure that the correct integrity test is carried out on that cable in accordance with the operating requirements. Arranged on the top surface of the unit 30 is an indicator 35, in this case an LED, which provides an indication to the tester as to whether the cables pass the test or not. In a preferred embodiment the indicator 32 may emit a green light if the cable is OK and emit no light if the cable is faulty. Alternatively, a red light may be emitted if the cable is found to be faulty.

Other variations may also be implemented to convey this information to the tester, which fall within the scope of the present invention. For example, the word "PASS" or the word "FAIL" could be illuminated depending on the outcome of the test.

The unit 30 also includes a transmitter coil test station 34 to enable the transmitter coils to be integrity tested. In the embodiment as shown in FIG. 2, the transmitter coil test station 34 is positioned on the upper surface of the unit 30 to allow a transmitter coil (not shown) to be placed thereon. The magnet of the transmitter coil to be tested aligns itself correctly on the transmitter coil test station 34 via another attracting magnet arranged within the unit 30, just below the surface of the unit, so that the attracting force of the magnets maintains the transmitter correctly in place for testing. As is shown in FIG. 2, the transmitter coil test station 34 may include indicia means 36, such as a pictorial representation of a transmitter coil that is to be placed correctly upon the test station 34. By placing the transmitter coil to be tested over this indicia means 36, the transmitter coil is automatically placed in the appropriate area on the test station 34 for testing.

Once the coil has been placed upon the test station 34 it is connected via a cable to a connecting socket 31 of test station 32. As the coil to be tested is designed to receive only one type of cable and the cable plug will only fit one of the connecting sockets 34 on test station 32, the unit 30 can then determine the type of coil being tested and can access the appropriate test parameters from its stored memory device (discussed in more detail below).

The testing unit 30 also includes an on/off switch 37 and may also include various indicia means which may aid the tester in using the unit. Such indicia means may include graphics grouping the sockets together and marking them with descriptive text indicating which cables they relate to, as well as similar labelling for the transmitter coil test station indicating the type of coil to be tested.

Figure 3:
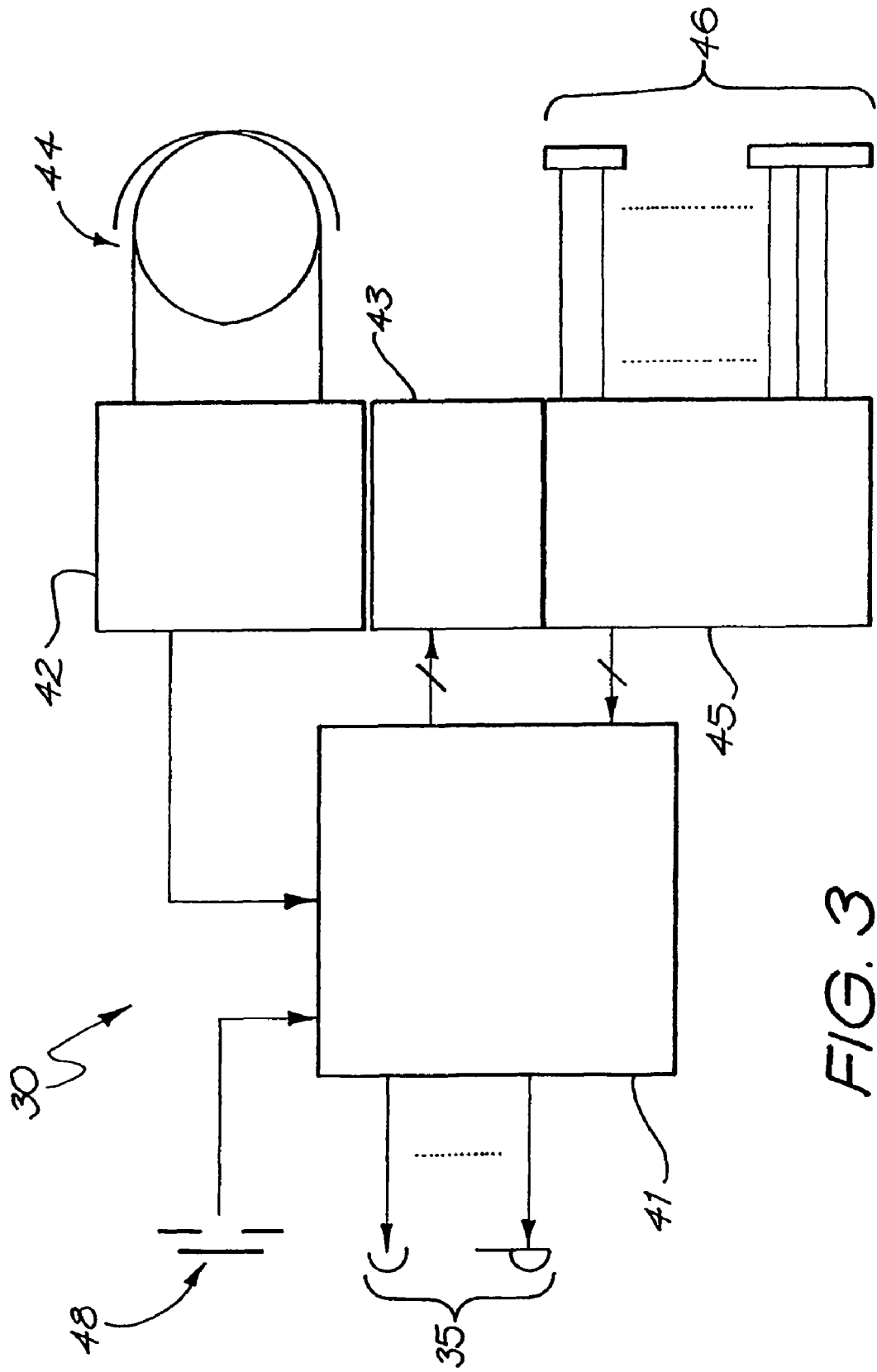
FIG. 3 is a block functional diagram of the tester unit of the present invention.

FIG. 3 is a functional block diagram of one embodiment of a tester unit 30 showing how the system operates in a functional mode. The tester unit 30 can be considered to consist of a microcontroller 41, a receiver coil voltage rectification and current sensing circuit 42, a receiver coil 44, a socket voltage driver 43, a cable test circuit 45, a series of sockets 46, a series of LEDs 35, and an on/off switch 48.

The microcontroller 41 is, in the depicted embodiment, a programmable microcontroller that essentially controls the application of test signals to the appropriate sockets at the appropriate times and also digitises and measures the appropriate measurement signals at the appropriate times. An Analogue to Digital Converter (ADC) is built into the microprocessor 41 to digitise the measurements, and the microprocessor 41 contains software to compare the measured values to the known limits which have previously been established for the coil and/or cable being tested and which are stored within a memory of the microprocessor 41.

The receiver coil voltage rectification and current sensing circuit 42 essentially consists of a circuit that measures a parameter related to the receiver coil current and a rectified voltage inductively induced in the receiver coil 44 when it is in close proximity to and aligned with the transmitter coil being tested.

The socket voltage driver 43 activates the sockets and allows the testing of both the coils and cables to be undertaken by providing each socket with the required voltage as dictated by the microcontroller 41.

The cable test circuit 45 monitors the functionality of the cables being tested by sensing the current being passed therethrough.

The series of sockets 46 allow the coils and/or cables to be connected to the test unit such that their operation can be tested. Under direction from the circuit 43, the sockets can be activated and the coil and/or cable tested.

The series of LEDs 35 provide indicators visible to the tester regarding whether the cables and/or coils being tested meet the requirements. This could include one LED representing a PASS, or a series of LEDs representing a PASS and/or a FAIL.

The on/off switch 48 toggles the power to the system on or off.

The system will now be described in use, with reference to FIGS. 2, 3 and 4.

In order to test the operation of a particular transmitter coil, the coil is placed on the transmitter coil test station 34 where it is held in place by an alignment magnet that cooperates with the magnet of the transmitter coil. The alignment magnet is preferably arranged on the inside of the unit housing below the area marked for placement of the transmitter coil under test, this area being shown in FIG. 2 by reference numeral 36. The purpose of the alignment magnet is to ensure that the transmitter coil under test is located within a 1mm radius of its designed position. A cable is then connected from the transmitter coil to a provided socket, shown in FIG. 2 by reference numeral 31, the socket 31 matching the correct cable connector.

Once the coil and cable are in place, the microcontroller 41 can be activated to send a signal to the socket voltage driver 43 to drive the coil with an AC square wave voltage source at or near the resonant frequency of the coil. This resonant frequency is dependent on the type of coil being tested, for example in some instances it may be near 2.5 or 5.0 MHz. A simple push-pull square wave voltage driver circuit, similar to those used in external speech processors is adequate for this purpose and is shown in FIG. 4 by reference numeral 43.

If the coil/cable combination plugged into the device is correctly functioning, the circuit will resonate and the coil current will have a value determined by the coil impedance at its resonant frequency, which is typically a few tens of Ohms, or less. In testing the coil/cable combination in accordance with the present invention, the method involves monitoring the coil current and the rectified voltage induced in the receiver coil 44 close to and aligned with the coil being tested, and if the current and the rectified voltage is found to be outside an acceptable value range, the coil/cable combination passes the test and the device indicates a PASS to the tester via illuminating the LED 35. If the coil/cable combination is found to be faulty (eg. the coil cable is broken, connector faulty etc) the device indicates a fail by not illuminating the LED, or alternatively, by emitting a FAIL signal via another indicator device.

In the event of a failure, most coil/cable combinations either involve a complete failure of the circuit or a detuning of the circuit in some way. Therefore in these fault conditions, the amplitude of the coil current will be reduced below a predetermined threshold and the coil will be detected as having failed.

The Receiver Coil Voltage Rectification and Current Sensing Circuit 42 measures the compliance of the coil/cable combination and outputs the result to the microcontroller 41. As mentioned above, one way to test the coil involves monitoring the current, and this can be done in a number of different ways.

Figure 4:
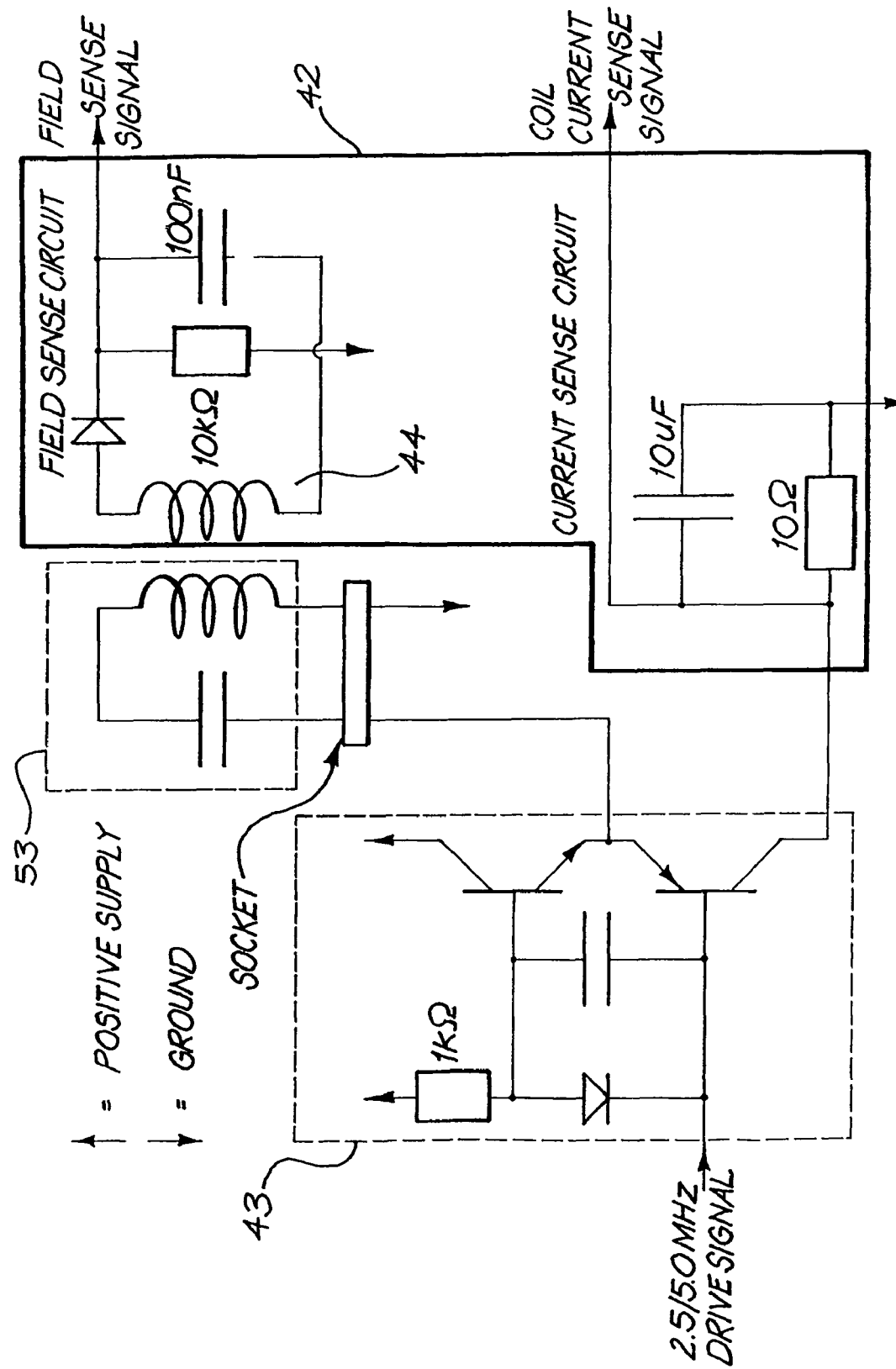
FIG. 4 is a circuit diagram showing a circuit capable of testing a coil/cable combination according to one embodiment of the present invention.

FIG. 4 depicts a circuit suitable for this purpose in accordance with a preferred embodiment. In FIG. 4, the socket voltage driver is shown as 43, the Receiver Coil Voltage Rectification and Current Sensing Circuit is shown as 42, the coil being tested is shown as 53, and the receiver coil is shown as 44.

The microprocessor (not shown in FIG. 4) produces a crystal controlled AC drive signal at or near the resonant frequency of coil 53 (as described above). This signal controls the socket voltage driver circuit 43, which consists of a simple push-pull driver as shown. AC current flowing in the coil 53 induces a mean voltage across the 10 ohm resistor of the Current Sensing Circuit 42, and this voltage is smoothed by the 10 uF capacitor. This smoothed voltage is then sent to the microprocessor 41, being representative of the coil current sense signal.

The field sense circuit of the Receiver Coil Voltage Rectification and Current Sensing Circuit 42 includes a multi-turn coil 44 which is in close proximity to the coil 53 under test. The AC current flowing in the coil 53 induces an AC voltage in the adjacent receiver coil 44, and this voltage is also rectified and smoothed by the remainder of this circuit and is sent to the microcontroller 41, being representative of the field sense signal.

Once the Receiver Coil Voltage Rectification and Current Sensing Circuit 42 has taken the measurements representative of the coil current sense signal and the field sense signal, the microprocessor utilises stored software to determine whether or not the values measured for the coil, correspond to the desired range of values within the design specification of that particular coil. If these values do fall within the design specification range for that coil, a signal is sent to the LED 35 to illuminate and so convey to the user that the device has passed the test. Otherwise, either a FAIL signal will be conveyed to the user or the LED 35 will not be illuminated, which is indicative of a FAIL.

Figure 5:
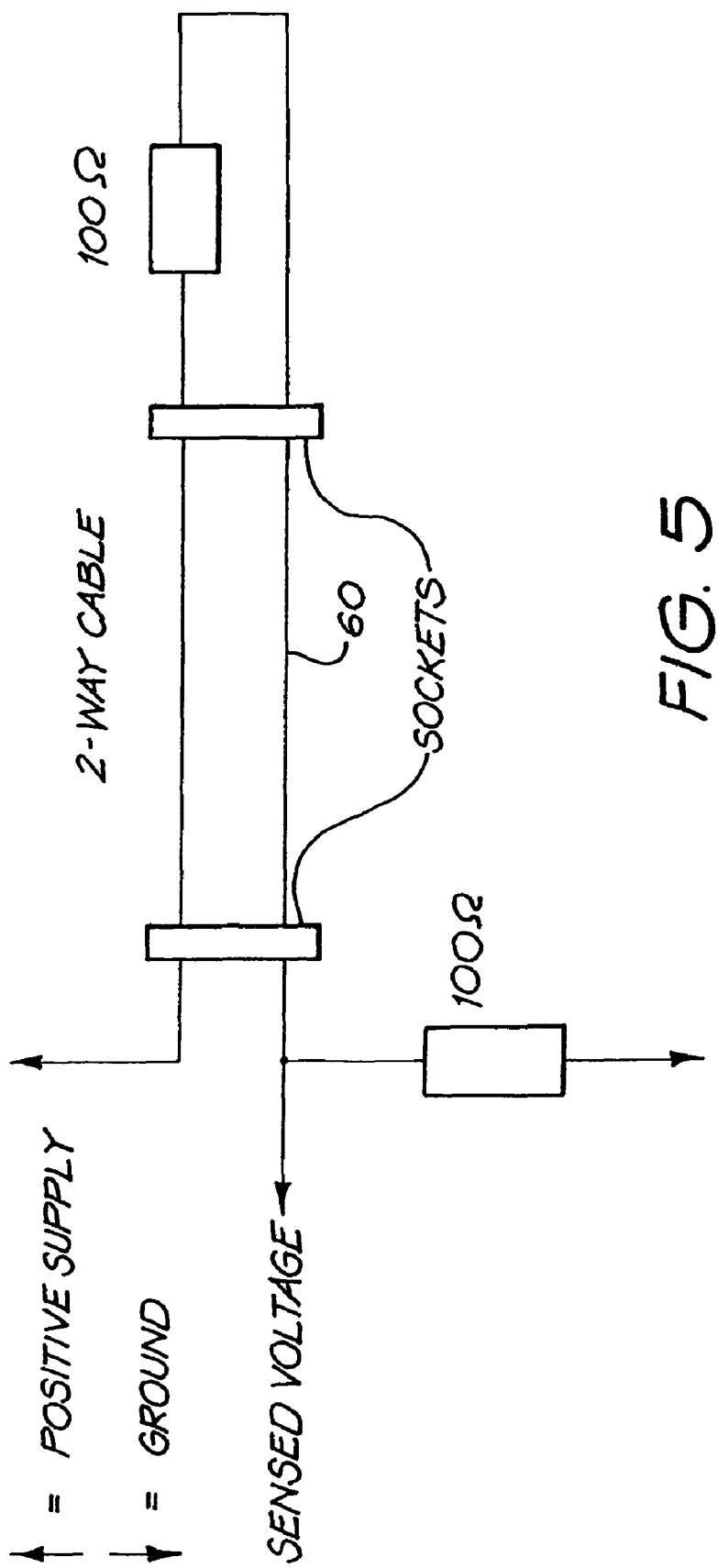
FIG. 5 is a circuit diagram showing a circuit capable of testing a cable according to one embodiment of the present invention.

FIG. 5 shows a circuit for testing the compliance of a cable only, according to an embodiment of the present invention. In this embodiment, measurements are made by placing a DC potential on one cable lead and measuring the potential on another. The other end of the cable is plugged into a resistor load network connecting all the cable leads together. When all the cable's leads are functioning normally a specific voltage, determined by the resistor load network, is expected on the sensed lead 60. If a fault occurs (one line open circuit or shorted to another) this will change the current flow in the cable and cause the voltage in the sensed lead 60 to change. The voltage is sensed by digitising it using the microprocessor 41 ADC and software is used to determine whether the sensed value corresponds to a normal or a faulty cable. When a voltage is sensed which corresponds to a normal cable the microprocessor 41 illuminates the "PASS" LED 35 in the manner as discussed above.

FIG. 5 depicts a test undertaken on a typical two lead cable. In this example, if the cable is normal (ie. both leads connected and not shorted), the two resistors create a potential divider and the sensed voltage is equal to 50% of the supply voltage. If either lead is open circuit the sensed voltage becomes equal to ground. If the leads are shorted the sensed voltage is equal to the supply rail voltage. A similar arrangement can be used for cables with 3 or more leads.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An apparatus for testing components of a medical device comprising a cable detachably coupled to a transmitter coil, the testing apparatus comprising:

a plurality of cable testing stations each configured to electrically connect to an end of the cable;

a coil testing station configured to inductively connect to the transmitter coil; and a testing circuit coupled to said plurality of cable testing stations and to said coil testing station configured: to drive the transmitter coil via one of said cable testing stations to concurrently test the cable and the transmitter coil when the cable is connected to said one of said cable testing stations and the transmitter coil is inductively connected to said coil testing station, and to test the cable independent of the transmitter coil when opposing ends of the cable are connected to two of said cable testing stations, the apparatus configured to indicate the response of the coil and cable, or the cable itself to the respective test.

2. The testing apparatus of claim 1, wherein the plurality of cable testing stations comprise a first cable testing station configured to be electrically connected to a first type of cable end, and a second cable testing station configured to be electrically connected to a second type of cable end.

3. The testing apparatus of claim 2, wherein the first cable testing station comprises a socket configured to receive a plug of one of two or more types of cables.

4. The testing apparatus of claim 1, wherein the coil testing station comprises a planar area configured to receive the transmitter coil.

5. The testing apparatus of claim 4, wherein the testing apparatus is configured to sense the type of the transmitter coil when the coil is disposed on the planar area.

6. The testing apparatus of claim 5, wherein the testing circuit is further configured to access from a memory component of the appropriate stored data for the sensed coil type.

7. The testing apparatus of claim 1, wherein the coil testing station comprises a receiver coil configured to be inductively coupled to the transmitter coil.

8. The testing apparatus of claim 7, wherein the planar area has an indicator disposed thereon that provides an indication of where the transmitter coil should be positioned for coupling to the receiver coil.

9. The testing apparatus of claim 8, wherein the indicator is a pictorial representation of the transmitter coil.

10. The testing apparatus of claim 7, wherein the testing circuit is configured to induce a voltage in the receive coil, and to determine whether a smoothed voltage corresponding to the induced voltage falls within a design specification range for the transmitter coil.

11. The testing apparatus of claim 1, wherein a magnet is disposed adjacent the transmitter coil, and wherein the coil testing station comprises a magnet configured to provide magnetic alignment with magnet disposed adjacent the transmitter.

12. The testing apparatus of claim 1, further configured to sense the type of the cable when the cable is electrically connected to the testing apparatus, and configured to access stored data for the sensed cable type from a memory component.

13. The testing apparatus of claim 1, wherein the testing circuit further comprises a control circuit configured to control the operations of the testing apparatus.

14. The testing apparatus of claim 13, wherein the control circuit is a microcontroller.

15. The testing apparatus of claim 14, wherein the microcontroller comprises a microprocessor having an analog to digital converter (ADC) configured to digitize a voltage in the cable when the at least one testing circuit tests the cable.

16. The testing apparatus of claim 1, wherein the testing circuit further comprises a memory component.

17. The testing apparatus of claim 1, further comprising an output component for outputting a result of the tests.

18. The testing apparatus of claim 17, wherein said output component comprises a light.

19. The testing apparatus of claim 18, wherein the light is a light emitting diode (LED).

20. The testing apparatus of claim 1, wherein the medical device is a cochlear implant system.

21. A method of testing components of a medical device comprising a cable detachably coupled to a transmitter coil, the testing performed with a testing apparatus comprising a plurality of cable testing stations each configured to electrically connect to an end of the cable, a coil testing station configured to inductively connect to the transmitter coil, a testing circuit and a receiving coil the method comprising:
  driving, with the testing circuit, the cable and transmitter coil via a first cable testing station so as to induce a voltage in the receiver coil of the apparatus to concurrently test the cable and the transmitter coil; the testing apparatus indicating a response to the test; and
  driving, with the testing circuit, a test signal through the cable independent of the transmitter coil when opposing ends of the cable are connected to two of said cable testing stations, the test apparatus indicating a response to the test.

22. The method of claim 21, further comprising:
  measuring a response of one or more of the cable and the transmitter coil to the test signal; and
  evaluating the measured response of the one or more cable and transmitter coil.

23. The method of claim 21, further comprising:
  rectifying and smoothing the voltage induced in the receiver coil; and
  determining whether the rectified and smoothed voltage falls within a design specification range for the transmitter coil.

24. The method of claim 21, further comprising:
  sensing the type of the cable; and
  sensing the type of the transmitter coil.

25. The method of testing of claim 24, further comprising:
  retrieving data corresponding to the sensed type of the cable and the coil.

26. The method of claim 21, wherein the coil testing station and the transmitter coil each comprise magnets, and wherein the method further comprises:
  magnetically coupling the transmitter coil to the coil testing station.

* * * * *